US005231088A

United States Patent [19]

Mikami et al.

[11] Patent Number: 5,231,088

[45] Date of Patent: Jul. 27, 1993

[54] CHEMICALS FOR PROTECTION OF PLANT AND REMOVAL OF PLANT VIRUS, AND PRODUCING METHOD THEREOF

[75] Inventors: Yoichi Mikami, Tokyo; Michiko Aoki, Kanagawa; Motomu Tan, Tokyo; Kuniaki Ono, Tochigi; Susumu Kubo, Kanagawa; Tadaharu Hieda; Atsushi Fukushima, both of Kanagawa, all of Japan

[73] Assignee: Japan Tobacco, Inc., Tokyo, Japan

[21] Appl. No.: 898,164

[22] Filed: Jun. 12, 1992

Related U.S. Application Data

[63] Continuation of Ser. No. 536,542, Jul. 6, 1990, filed as PCT/JP89/00021, Jan. 11, 1989 abandoned.

[30] Foreign Application Priority Data

| | | | |
|---|---|---|---|
| Jan. 12, 1988 | [JP] | Japan | 63-3121 |
| Jan. 12, 1988 | [JP] | Japan | 63-3122 |
| Jan. 12, 1988 | [JP] | Japan | 63-3123 |

[51] Int. Cl.[5] .......... C08B 37/00

[52] U.S. Cl. .......... 514/54; 536/123.1; 435/101; 435/911

[58] Field of Search .......... 536/1.1; 514/54; 435/101, 911

[56] References Cited

U.S. PATENT DOCUMENTS 4,051,314 9/1977 Ohtsuka et al. .......... 435/101

OTHER PUBLICATIONS

J. Stenesh, *Dictionary of Biochemistry*, p. 74.

*Primary Examiner*—Ronald W. Griffin
*Assistant Examiner*—Pamela S. Webber
*Attorney, Agent, or Firm*—Beveridge, DeGrandi, Weilacher & Young

[57] ABSTRACT

This invention relates to a chemical for protection of plants and removal of plant viruses and its producing method, which is applicable to the prevention of viral disease in the fields of agriculture and horticulture.

That is, this invention relates to a chemical for protection of plants and removal of plant viruses which contains a plant virus prevention active substance as its effective ingredient and which was cultivated using a fungus selected from the genus Fomes and was produced in fungi or medium.

6 Claims, 11 Drawing Sheets

CHEMICALS FOR PROTECTION OF PLANT AND REMOVAL OF PLANT VIRUS, AND PRODUCING METHOD THEREOF

This application is a continuation, of application number 07/536,542, filed Jul. 6, 1990, filed as PCT/JP89/00021, Jan. 11, 1989, now abandoned.

TECHNICAL FIELD

This invention relates to the chemicals for a plant protection and virus removal which can be used in the protection of plants and removal of plant viruses in the field of agriculture and gardening, and it relates also to the producing method of said chemicals.

BACKGROUND ART

Tobacco, green peppers, tomatoes, cucumbers and watermelons, and the like, which are cultivated in the field, in the paddy field and in greenhouses, are often damaged by tobacco mosaic virus (hereinafter referred to as TMV), cucumber mosaic virus, cucumber green-spot mosaic virus and potato Y virus, etc.

These viruses also exist in other crops, such as weeds, seeds and seedlings and in soil. They are contagious and are often carried by juice sucking insects, and the like.

Previously, soil disinfection and insecticides were used as countermeasures for plant protection and removal of crop viruses. These countermeasures, however, were mainly an indirect means of protection and technical methods of virus removal.

There are a few direct plant protection and virus removal chemicals which are called "sodium alginic acid" (Japan Patent No. 717594, the Ministry of Agriculture, Forestry and Fisheries Registered No. 13440) and culture extract of *Lentinus edodes* (Japan Patent No. 1012014, the Ministry of Agriculture Forestry and Fisheries Registered No. 15584). However, neither of these effect systemically; therefore, they are incapable of moistening the entire plant, and it is necessary to scatter them all over the plant. In addition, their effectiveness in the field is not very high.

On the other hand, protein, which is found in the marvel-of-Peru, has recently been popularized as an anti-viral plant substance which has actually systemic effectiveness [Japan TOKKYO-KOKAI-KOHO (18-month Publication of Unexamined Patent Application) SHOWA 60(1985)-243100 (hereinafter referred to as TOKKAISHO 60-243100)]. Unfortunately, however, production of this protein must comply with agricultural means or plant cell culture [Japan TOKKAISHO 61(1986)-5790]. Therefore, productivity is automatically limited, and it is impossible to provide it at low cost for mass production.

The present invention has improved on defects of the previous plant protection and virus removal chemicals on the market. The present invention has achieved more effective saturated shifting dominance, and a secure and valid chemical substance can be provided at low cost for mass production.

DISCLOSURE OF THE INVENTION

In order to achieve the aforementioned purposes, inventors have used a screen metabolic product material made from various microorganisms. As a result, it was found that a high molecular polysaccharide, which is produced in a culture material by a fungus belonging to the genus Fomes, shows remarkable anti-viral activity. Fungi belonging to the genus Fomes which are utilized in the present invention, are *Fomes fomentarius, Fomes geotropus, Fomes melanoporus*, etc. These culture solutions showed anti-viral activity, albeit at different degrees.

In addition, strains belonging to genus Fomes, which are utilized in the present invention are separated from the natural Fomes, or well-known preserved strains such as *Fomes formentarius* IFO 8246, IFO 30371, IFO 30777 (IFO stands for the Institute of Fermentation Organization) or *Fomes fomentarius ATCC* 26708, ATCC 34687, ATCC 46213 (ATCC stands for the American Type Culture Collection). *Fomes geotropus* ATCC 26709, *Fomes melanoporus* ATCC 26132, and others. Among them, the most preferable strain is *Fomes fomentarius* JTS 3046 (FERM-BP 2230) which has a remarkably high production of acid high molecular polysaccharides.

Incidentally, JTS 3046 strain, which was successively cultured from IFO 8246 strain as the parent strain, is obtained. This acid high molecular polysaccharide high productivity strain had been deposited as FERM P-9704 on Nov. 11, 1987 at the Fermentation Research Institute, Agency of Industrial Science and Technology, the Ministry of International Trade and Industry located in Ibaraki-ken, Japan. It was then transferred to the International Deposit there on Jan. 5, 1989, and is available for use under accession number, FERM BP-2230.

Contagion by TMV, etc. can be effectively prevented by sprinkling stems and leaves of tobacco, tomatoes, green peppers, etc. with a dissolved culture filtrate of the cultured strain, a hydrothermal extract of the fungus or its active component, high molecular polysaccharide.

In particular, an anti-viral active material, which is produced by a strain belonging to genus Fomes and is different from previous well-known polysaccharides, has a remarkable effectiveness because it appears systemically on the treated plant.

Strains which are adapted to this invention can be placed or aggitatingly cultivated in medium used for the general cultivation of fungi. Effectiveness depends on the quantity of high molecular polysaccharide used as the active component, especially that of acid high molecular polysaccharide. The followings are detailed explanations of the results of experiments with this invention.

In the present invention, a high molecular polysaccharide can be obtained both fungi and culture filtrate by separate extraction. The larger quantity can be obtained from the culture filtrate after the fungi are produced from the culture of high molecular polysaccharide.

It is preferable to use a medium composed of general filamentary fungi with added yeast extracts, but any composed medium conducive to fungi growth can be used.

In the present invention, the medium, which contains glucose, peptone, yeast extract, malt extract, potassium phosphate, magnesium sulfate and tap water, was used for the culture of the high molecular polysaccharide productivity fungi.

Proper culture conditions call for 20° C.–30° C. temperature for the standing culture. In addition, shaking and aerating the culture are preferable, although any conditions are acceptable as long as they promote the growth of a high molecular polysaccharide for fungus production.

After the culture filtrate and fungi are obtained from the culture material of high molecular polysaccharide productivity fungi by use of the centrifuge separation method and filtering, the high molecular polysaccharide, which has anti-viral activity, is extracted therefrom.

Several methods can be used to extract a high molecular polysaccharide from the culture filtrate. These are dialysis, ultrafiltration, fractional precipitation, salting out, solvent partition, ion exchange chromatography, gel filtration chromatography, and absorption chromatography. These methods can be used individually or jointly in experimentation.

To extract a high molecular polysaccharide from the fungi, the same method used for the culture filtrate should be followed after solids are eliminated through use of hydrothermal extraction.

The active component remains inside the membranes when dialysis is used. A phenolic sulfate reaction and a carbazole sulfate reaction are positive, but the ninhydrin reaction is negative. Therefore, it is shown that the high molecular polysaccharide does not contain amino acid, proteins or amino sugar.

Furthermore, the active component is divided into the neutral polysaccharide, whose molecular weight is more than or equal to 0.1 million, and the acid polysaccharide whose molecular weight is less than 0.1 million. These polysaccharides can then measured by phenolic sulfate method.

Both polysaccharides show their effectiveness in plant protection and virus removal; however, systematic effectiveness is shown only by the acid high molecular polysaccharide.

In the present invention, a high molecular polysaccharide is generally cultivated by shaking it onto the medium which contains glucose, "evios" (trade name of the Evios Pharmaceutical Co.), potassium phosphate, magnesium sulfate and tap water. After the culture is completed, the culture filtrate can be obtained by filtering.

Next, the culture filtrate and the fungus hydrothermal extracted solution are diluted. Ethanol, in an amount twice as much as the diluted solution, is added to the diluted solution, and the sediment which is generated is then extracted.

This sediment is dissolved in water and is then added to trichloroacetic acid. After the new sediment such as protein, etc. is removed by the centrifuge separation method, dialysis shall be performed to make phosphoric acid buffer solution.

Ingredients in the dialysis membranes are absorbed into the ion exchange material which has a diethyl amino ethyl group, and then they are separately liquidized, gradually raising the concentration of NaCl.

The effluent is separated in fixed quantities, and the amount of sugar is measured using the phenolic sulfate method.

Contents of the each extracted liquid are analyzed by chromatography. The extracted liquid, which contains only high molecular polysaccharide as sugar, is then selected.

Again, ethanol is added to the liquid and removes proteins, etc. after removing the sediment. Dialysis is performed on ion exchanged water, and after freeze drying, a freeze dried high molecular polysaccharide can be obtained.

The freeze dried high molecular polysaccharide shall be purified by gel filtration chromatography, and finally a high molecular polysaccharide specimen salt is obtained.

In addition, cations are removed as much as possible from the high molecular polysaccharide specimen salt by ion exchange resin, and a high molecular polysaccharide specimen can be obtained.

Among these high molecular polysaccharides, a high molecular polysaccharide F-B is obtained by cultivating a high molecular polysaccharide F-B productive fungus, and a high molecular polysaccharide F-Ab is obtained by cultivating a high molecular polysaccharide F-Ab productive fungus. Both are novel high molecular polysaccharides and are shown physiochemically as follows:

(1) Elementary analysis

[High molecular polysaccharide F-B specimen salt]
C: 34.8%
H: 5.5%
N: 0.6%
Ash content: 11.6%

[High molecular polysaccharide F-B specimen]
C: 37.1%
H: 5.9%
N: 0.5%
Ash content: 5.2%

[High molecular polysaccharide F-Ab specimen salt]
C: 36.0%
H: 6.0%
N: 0.5%
Ash content: 9.0%

[High molecular polysaccharide F-Ab specimen]
C: 37.9%
H: 5.9%
N: 0.4%
Ash content: 3.9%

(2) Molecular weight

[High molecular polysaccharide F-B]

The results obtained by performing gel filtration chromatography are shown on FIGS. 1*a* and 2*a*.

Range of gel filtration method: 7,000–17,000
Mean molecular weight: 12,000

[High molecular polysaccharide F-Ab]

The results obtained by performing gel filtration chromatography are shown on FIGS. 1*b* and 2*b*.

Range of gel filtration method: 10,000–20,000
Mean molecular weight: 15,500–16,500

(3) Optical rotation

[High molecular polysaccharide F-B]

$[\alpha]_D^{25} = -39°$ (C=0.53%, Aqueous solution)

[High molecular polysaccharide F-Ab]

$[\alpha]_D^{25} = -34°$ (C=0.52%, Aqueous solution)

(4) Ultraviolet absorption spectrum

[High molecular polysaccharide F-B]

Shown as FIG. 3*a*

[High molecular polysaccharide F-Ab]

Shown as FIG. 3*b*

(5) Infrared absorption spectrum

[High molecular polysaccharide F-B]

Shown as FIGS. 4*a* and 5*a*

[High molecular polysaccharide F-Ab]

Shown as FIGS. 4*b* and 5*b*

[High molecular polysaccharides F-B, F-Ab]

These high molecular polysaccharide specimen salts are strongly absorbed at —$COO^-$ of 1612 $cm^{-1}$.

In addition, the high molecular polysaccharide specimens, which diminished cation by ion exchange resin, absorption of 1612 $cm^{-1}$ lessens, on the other hand, absorption of —COOH of 1725 $cm^{-1}$ is confirmed.

(6) Solubility to solvent

[High molecular polysaccharides F-B, F-Ab]

Both of these can be dissolved in water and dimethyl sulfoxide. However, neither can be dissolved in methyl alcohol, ethyl alcohol, acetone or ether.

(7) Color reaction

[High molecular polysaccharides F-B, F-Ab]

| | |
|---|---|
| Phenolic sulfate reaction | Positive (both) |
| Carbazole sulfate reaction | Positive (both) |
| Ninhydrin reaction | Negative (both) |

(8) Distinction of basic, acid and neutral

[High molecular polysaccharides F-B, F-Ab]

pH of 0.1% aqueous solution of high molecular polysaccharide specimens are both acid.

(9) Color

[High molecular polysaccharides F-B, F-Ab]

Both of these are white.

(10) Sugar composition and its formation

[High molecular polysaccharides F-B, F-Ab]

Each high molecular polysaccharide was hydrolyzed in 2N-trifluoroacetate for one hour at 121° C. As a result, glucose and glucuronic acid were detected by film chromatography which was used on upset plates.

Glucuronic acid in each high molecular polysaccharide was measured by the carbazole sulfate method (for example, T. Bitter, H. Muir, Anal. Biochem., 4, 330, 1962).

In addition, after each high molecular polysaccharide was hydrolyzed, it was deoxidized into alditol acetate in the usual way (e.g. comprehensive polysaccharide chemistry vol. I, p. 68. By Atsuya Harada, Takeo Koizumi; published by Kodan-sha 1973) and was analyzed by gas chromatography.

In this case, reactions to ninhydrine reagent were both negative, and neither amino acid nor amino sugar were detected.

[High molecular polysaccharide F-B]

As a result, the ratio of the composition of glucose to glucuronic acid was 3.4:1.

[High molecular polysaccharide F-Ab]

As a result, the ratio of the composition of glucose to glucuronic acid was 9:2.0–1.8.

(11) Detection of protein

[High molecular polysaccharides F-B, F-Ab]

Protein in a 0.1 ml solution was detected using the Lowry method, in which solution a 20 mg high molecular polysaccharide had been dissolved in 1 ml water. Protein was not detected and color was not formed.

(12) Detection of pyruvic acid

[High molecular polysaccharides F-B, F-Ab]

Hydrolysis materials of each high molecular polysaccharide were measured with a lactic acid measurement kit, which is produced by Bellinger-Manheim Co. However, pyruvic acid was not detected.

(13) Methylation analysis

[High molecular polysaccharide F-B]

(a) After the methylation of the high molecular polysaccharide F-B, it was hydrolyzed to alditol acetate. The following result was obtained by using gas chromatography analysis:

1,5-di-O-acetyl-2,3,4,6-tetra-O-methyl glycitol: 1,3,5-tri-O-acetyl-2,4,6-tri-O-methyl glycitol: 1,5,6-tri-O-acetyl-2,3,4-tri-O-methyl glycitol: 1,3,5,6-tetra-O-acetyl-2,4-di-O-methyl glycitol=1:1.5:4:2

(b) Residue of the glucuronic acid in the high molecular polysaccharide was reduced to obtain the residue of the glucose in the usual way (e.g. H. Minakami et al., Agric. Biol. Chem., 48, 2405–2414, 1984). Then, the residue was methylated and hydrolyzed into alditol acetate. The following result was obtained by using gas chromatography analysis.

1,5-di-O-acetyl-2,3,4,6-tetra-O-methyl glycitol: 1,3,5-tri-O-acetyl-2,4,6-tri-O-methyl glycitol: 1,5,6-tri-O-acetyl-2,3,4-tri-O-methyl glycitol: 1,3,5,6-tetra-O-acetyl-2,4-di-O-methyl glycitol=2:3:4:2

[High molecular polysaccharide F-Ab]

(a) High molecular polysaccharide F-Ab was methylated, and then hydrolyzed into alditol acetate. The following result was obtained by using gas chromatography analysis.

1,5-di-O-acetyl-2,3,4,6-tetra-O-methyl glycitol: 1,3,5-tri-O-acetyl-2,4,6-tri-O-methyl glycitol: 1,5,6-tri-O-acetyl-2,3,4-tri-O-methyl glycitol: 1,3,5,6-tetra-O-acetyl-2,4-di-O-methyl glycitol=1:2:4:2

(b) Residue of glucuronic acid in the high molecular polysaccharide F-Ab was reduced to obtain residue of glucose in the usual way (e.g. H. Minakami, et al., Agric. Biol. Chem., 48, 2405–2414, 1984). Then, the residue was methylated and hydrolyzed into alditol acetate. The following result was obtained by using gas chromatography analysis.

1,5-di-O-acetyl-2,3,4,6-tetra-O-methyl glycitol: 1,3,5-tri-O-acetyl-2,4,6-tri-O-methyl glycitol: 1,5,6-tri-O-acetyl-2,3,4-tri-O-methyl glycitol: 1,3,5,6-tetra-O-acetyl-2,4-di-O-methyl glycitol=2:3:4:2

The chemicals for protection of plants and removal of plant viruses according to the present invention have shown great effectiveness in prevention and removal of plant viruses. Its effectiveness shown prominent saturated shifting dominance.

In addition, the chemicals for protection of plants and removal of plant viruses according to the present invention can be provided at low cost for mass production because it is easily produced in the fermentation industry by cultivating fungi.

BEST MODE FOR CARRYING OUT THE INVENTION

Figure 1A:
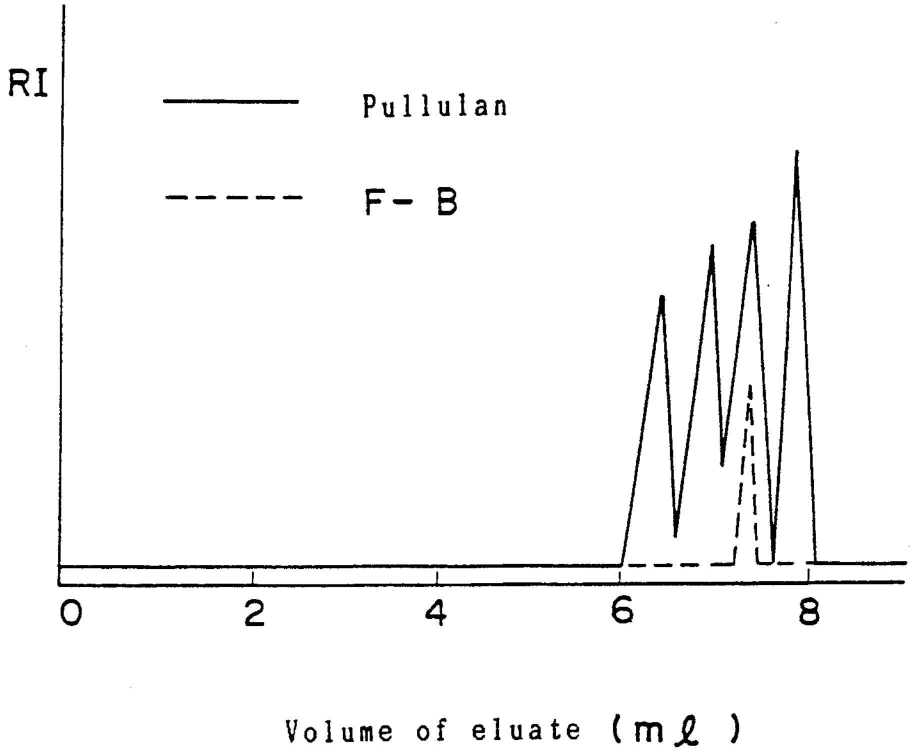
FIG. 1*a* shows the gel filtering chromatogram of the high molecular polysaccharide F-B in using TSK gel G3000 PWXL column. In the figure, a solid line shows molecular weight standard material pullulan, and a dotted line shows high molecular polysaccharide F-B.

The present invention is further explained detailedly by the following examples, however the present invention is not limited to these examples.

(1) Culture of Fungi

Inoculated *Fomes fomentarius* JTS 3046 strain (FERMBP 2230) on medium of potatoes, glucose and Japanese gelatin in a test tube, and cultivated the fungi for 10 days at 28° C. to preserve it.

This stock strain was inoculated on 100 ml of the following Medium A in a triangle flask with a capacity of 500 ml. It was then cultivated by rotating and shaking for 10 days at 28° C. at 200 r.p.m., and was then preserved as seed fungi.

| Medium A | |
|---|---|
| Glucose | 50 g |
| Peptone | 2 g |
| Yeast extract | 2 g |
| Malt extract | 10 g |
| $KH_2PO_4$ | 5 g |
| $MgSO_4$—$7H_2O$ | 2.5 g |
| Tap water | 1000 ml |

One hundred milliliters of seed fungi culture material was homogenized in a mixer. Sixty milliliters of the 100 ml of seed fungi culture material is inoculated on 1000 ml of the following Medium B in a triangle flask with a capacity of 3 liters. It was then cultivated by rotating and shaking for 10 days at 28° C. at 200 r.p.m. to obtain fungi culture material.

| Medium B | |
|---|---|
| Glucose | 50 g |
| Evios | 6 g |
| $KH_2PO_4$ | 2 g |
| $MgSO_4$—$7H_2O$ | 1 g |
| Tap water | 1000 ml |

Other strains such as *Fomes fomentarius* IFO 8246, IFO 30371, ATCC 26708, etc. are cultivated in the same way to obtain the fungi culture material.

(2) Preprocess of Purification

Eight liters of fungi culture material of *Fomes fomentarius* JTS 3046 strain, which were obtained in (1) above, were filtered by using Toyo filter paper No. 5C. (Eight 3-liter triangle flasks were used.) Fungi and culture filtrate were obtained.

Water, five times the amount of fungi, was added to the fungi, and the solution was heated for 10 minutes at 60° C. to extract liquid.

Sixteen thousand milliliters of ethanol was added to 8000 ml of culture filtrate and extracted liquid, and the solution was left for two days at 10° C. until precipitate appeared. The precipitate was separated from the solution by the centrifuge separation method.

The precipitate was then added to 800 ml of water and was used as a solution.

To the solution was added 40% (w/v) of 240 ml of trichloroacetic acid solution, and after agitation it was left overnight at 10° C. To remove precipitate such as protein, etc. which appeared, a centrifuge separation method was used for 15 minutes at 12000 r.p.m., and the supernatant liquid was collected.

The supernatant liquid was put on the dialysis membrane (spectrobore 3) and repeatedly equilibrated with 10 mM phosphate buffer solution (pH 6.0).

The inner solution in the dialysis membranes was absorbed into a cartridge type Zeta-Prep 100 DEAE (produced by LKB) which had a diethyl amino ethyl group after loading, and then the inside of the tube was rinsed with 3000 ml of a 10 mM phosphate buffer solution.

Most of the neutral high molecular polysaccharide F-N was not absorbed into the tube, but was just liquefied.

Next, to raise the concentration of NaCl from 0 to 400 mM linearly, 1500 ml of effluent was extracted at the rate of 25 ml/min.

Using a fraction collector, the effluent was separated into 10 ml quantities in test tubes. The sugar quantity in the extracted liquid in each tube was measured using the phenolic sulfate method.

In addition, the purity of the extracted liquid in each tube was examined by high-speed liquid chromatography applied to Toso's TSK gel G3000 PW column.

Liquid which contained the same ingredients was examined by gel filtering chromatography using Asahipak GS-510, and the molecular weight distribution was measured.

At the same time, the purity of each ingredient was examined by film chromatography using upset plate.

Figure 6:
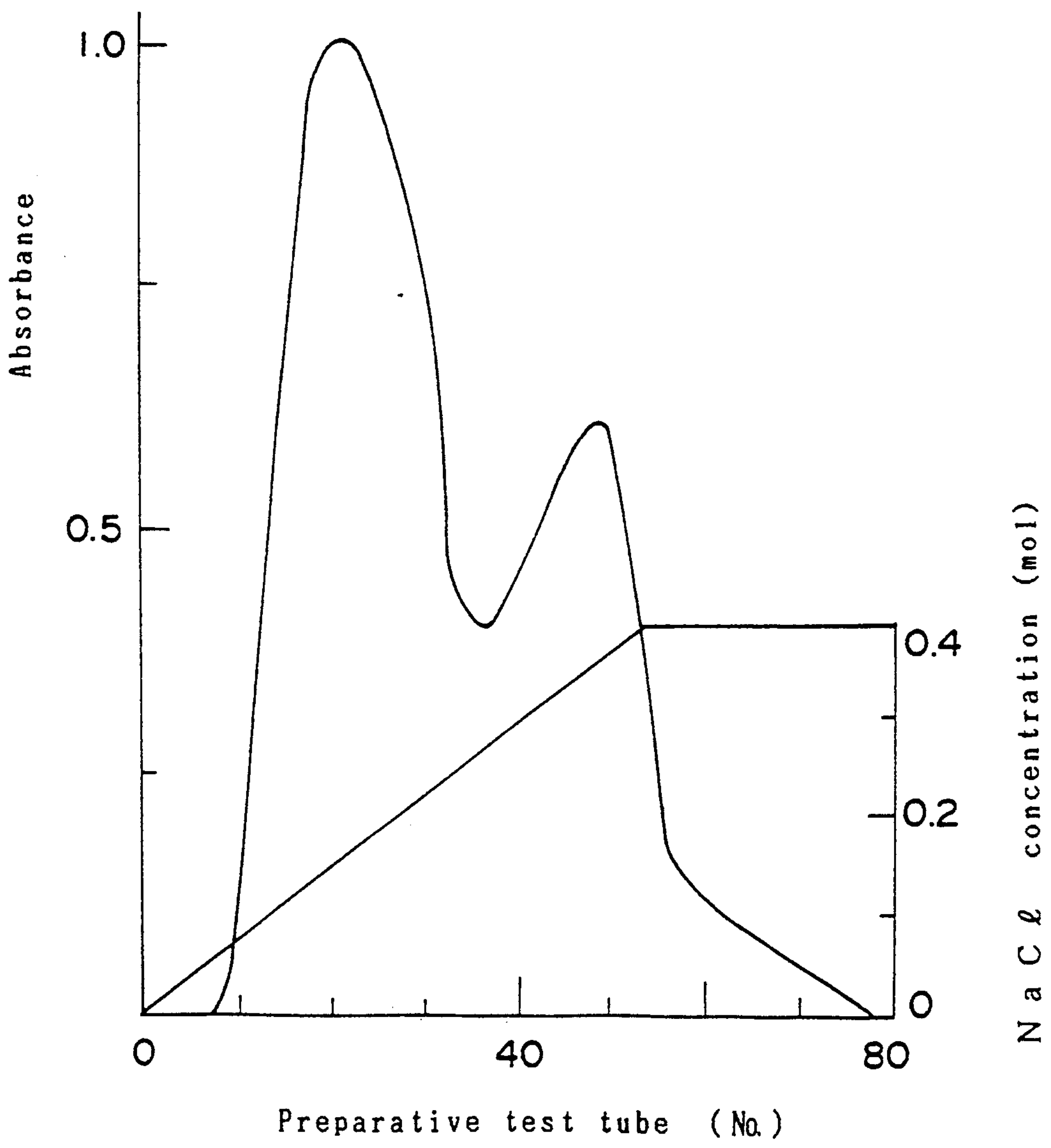
FIG. 6 shows the solubility curve for absorption of the high molecular polysaccharide, from which the culture material of *Fomes fomentarius* JTS3046 strain ZETA-Prep 100 DEAE column is obtained. Raising the NaCl concentration from 0 to 400 mM linearly, separating the solution, and using some sugar in the extracted liquid, is measured and then plotted.

The fixed quantity value of each extracted liquid which was detected by the phenolic sulfate method was plotted as shown on FIG. 6.

Extracted liquid in test tubes No. 8 to No. 11 contained neutral high molecular polysaccharide F-N.

Extracted liquid in test tubes No. 12 to No. 19 contained neutral high molecular polysaccharide F-N and acid high molecular polysaccharide F-Ab.

Extracted liquid in test tubes No. 20 to No. 27 contained acid high molecular polysaccharide F-Ab.

Extracted liquid in test tubes No. 28 to No. 42 contained acid high molecular polysaccharides F-Ab and F-B.

Extracted liquid in test tubes No. 43 to No. 56 contained acid high molecular polysaccharide F-B.

Extracted liquid in test tubes No. 57 to No. 62 contained acid high molecular polysaccharides F-B and F-C.

Extracted liquid in test tubes No. 63 to No. 76 contained acid high molecular polysaccharide F-C.

(3) Process of purification of high molecular polysaccharide F-B

Extracted liquid from test tubes No. 43 to No. 56 which was obtained in (2) above was collected. Ethanol in an amount 0.8 times the quantity of the extracted liquid was then added to the liquid. The solution was left overnight at 10° C. and the supernatant liquid was collected using a centrifuge separation method.

Ethanol in a quantity 0.7 times as much as the extracted liquid was added to the supernatant liquid, and precipitated polysaccharide was collected. Even protein, which appeared in an extremely small amount, was completely removed.

The collected polysaccharide was put in a tube for dialysis and was dialyzed for two days in ion exchange water.

After dialysis was completed, the solution was freeze dried, and 600 mg of freeze dried high molecular polysaccharide F-B specimen was obtained.

The high molecular polysaccharide F-B freeze dried specimen was used to obtain 500 mg of high molecular polysaccharide F-B specimen salt by using LC-09 model type extracted liquid chromatography which is produced by the Japan Analysis Industry and which has columns. These Asahipak GS-510 columns are connected to GS-320 in a series.

Culture materials of the other strains such as *Fomes fomentarius* IFO 8246, IFO 30371, ATCC 26708, etc. were purified in the same way, and high molecular polysaccharide F-B specimen and specimen salt were obtained.

(4) Process of purification of high molecular polysaccharide F-Ab

Extracted liquid from test tubes No. 20 to No. 27 which was obtained in (2) above was collected. Ethanol in an amount 0.8 times the quantity of the extracted liquid was then added to the liquid. The solution was left overnight at 10° C. and the supernatant liquid was collected using a centrifuge separation method.

Ethanol, in a quantity 0.7 times as much as the extracted liquid, was added to the supernatant liquid, and precipitated polysaccharide was collected. Even protein, which appeared in an extremely small amount, was completely removed.

The collected polysaccharide was put in a tube for dialysis and was dialyzed for two days in deionized water.

After dialysis was completed, the solution was freeze dried, and 600 mg of freeze dried high molecular polysaccharide F-Ab specimen was obtained.

The high molecular polysaccharide F-Ab freeze dried specimen was used to obtain 500 mg of high molecular polysaccharide F-Ab specimen salt by using LC-09 model type extracted liquid chromatography, which is produced by the Japan Analysis Industry and which has columns. These columns have Asahipak GS-510 which is connected to GS-320 in a series.

Culture materials of the other strains such as *Fomes fomentarius* IFO 8246, IFO 30371, ATCC 26708, etc., were purified in the same way, and high molecular polysaccharide F-Ab specimen and specimen salt were obtained.

(5) Chemical properties of high molecular polysaccharide

[High molecular polysaccharide F-B]

Figure 4A:
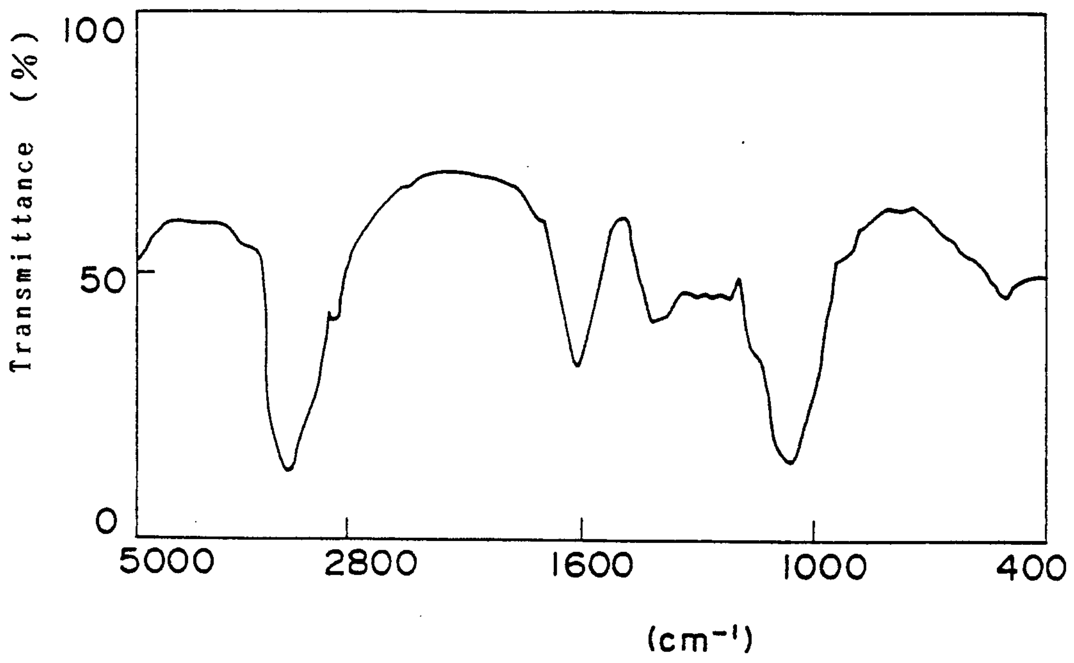
FIG. 4*a* shows the infrared absorption spectrum of the high molecular polysaccharide specimen salt F-B.

The infrared absorption spectrum of the high molecular polysaccharide F-B specimen salt which was obtained in (3) above, as shown on FIG. 4*a*, showed the strong absorption of $-COO^-$ of 1612 $cm^{-1}$ and contained cation such as sodium ion.

Removing cation from the high molecular polysaccharide F-B specimen salt through an ion exchange resin column, the absorption of 1612 $cm^{-1}$ lessened; on the other hand, that of the $-COOH$ of 1725 $cm^{-1}$ was apparently shown.

Figure 5A:
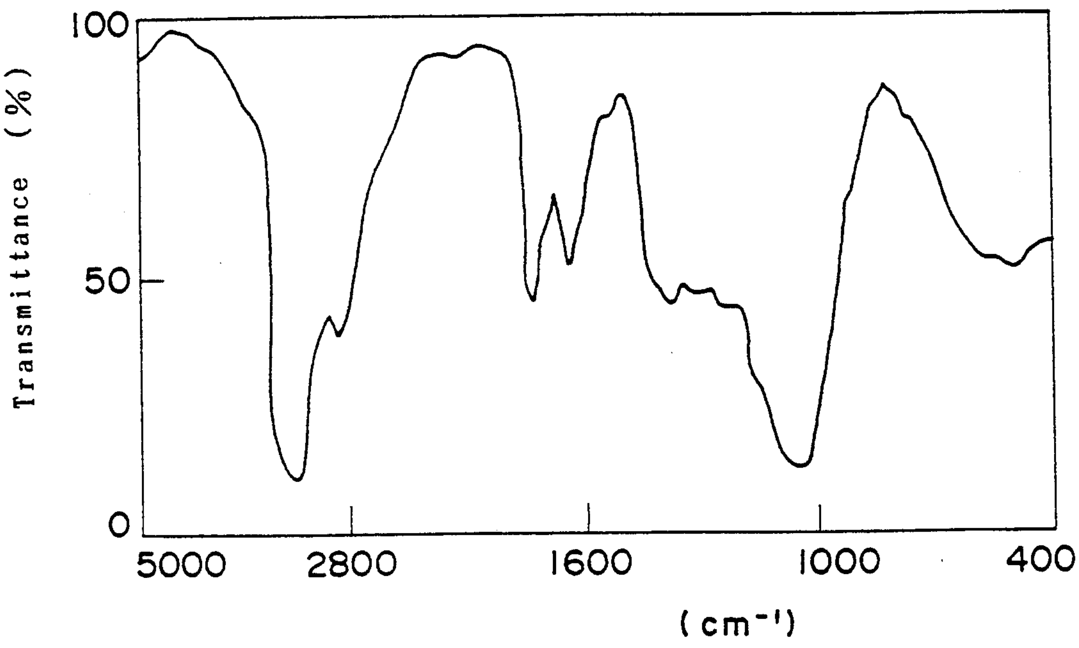
FIG. 5*a* shows the infrared absorption spectrum of the high molecular polysaccharide specimen F-B.

According to the infrared absorption spectrum, however, it is quite difficult to remove cation completely. Therefore, the purified specimen, as shown in FIG. 5*a*, was assumed to be a high molecular polysaccharide F-B specimen.

The specimens obtained are apparently confirmed as a single material as a result of the aforementioned variety of chromatography. They were all white and became transparent when dissolved in water.

(a) Elementary Analysis

Analytical results of high molecular polysaccharide F-B specimen salt which was obtained from the culture material for *Fomes fomentarius* JTS 3046 strain in (2) and (3) above are as follows.

C: 34.8%
H: 5.5%
N: 0.6%
Ash content: 11.6%

Analytical results of high molecular polysaccharide F-B specimen are as follows.

C: 37.1%
H: 5.9%
N: 0.5%
Ash content: 5.2%

In the above analysis, if the same tested samples are used, the values of N and Ash content often fluctuated. In this fluctuation, the values of C and H also fluctuated slightly.

It is assumed that the fluctuation of the quantity of Ash content, such as the ammonium ions and the sodium ions which combine to form salt, differed in every purification because high molecular polysaccharide F-B is acidic material.

In addition, because of the removal rate of cation by ion exchange resin changes in every experiment, the complete removal of N and Ash content could not be performed.

(b) Molecular weight determination

Figure 2A:
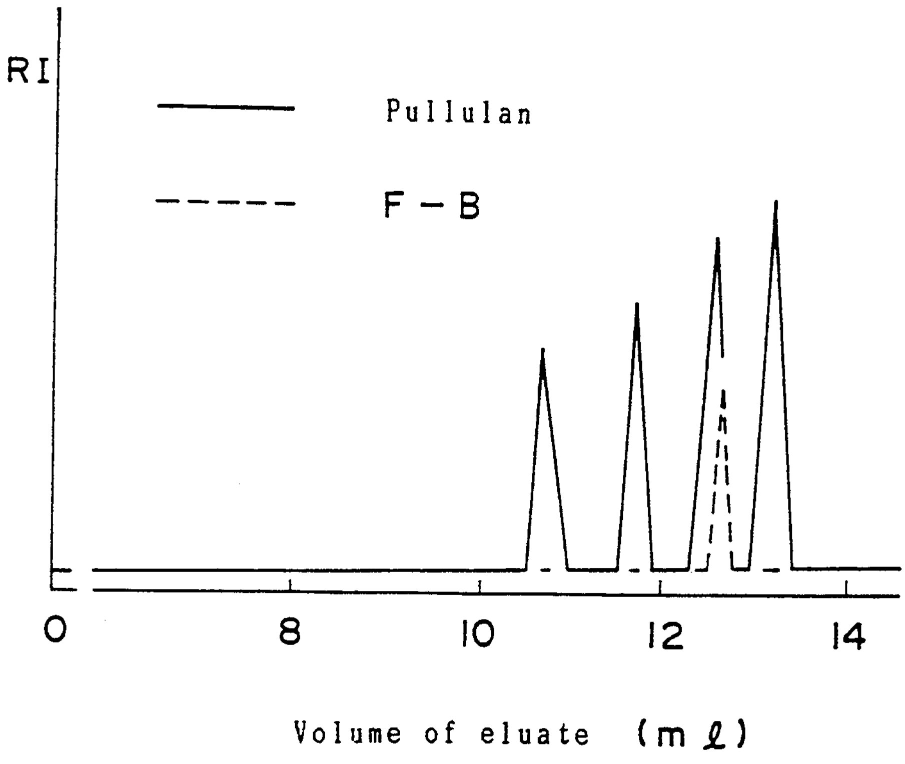
FIG. 2*a* shows the gel filtering chromatogram of the high molecular polysaccharide F-B in using Asahipak GS-510 column. In the figure, a solid line shows molecular weight standard material pullulan, and a dotted line shows high molecular polysaccharide F-B.

Test results of molecular weight of high molecular polysaccharide F-B, which was obtained from *Fomes fomentarius* JTS 3046 strain by gel filtration chromatography are shown on FIGS. 1*a* and 2*a*. Toso's TSK gel G3000 PWXL column or Asahikasei's Asahipak GS-510 column are equipped with high-speed liquid chromatography (attached to RI detector) and used pullulan as the standard molecular weight material (Pullulan Shodex STANDARD P-82; produced by Showadenko Co., Ltd.).

The distribution range of molecular weight by a gel filtration method was 7000–17000, and the mean molecular weight was 12000 using the former column. The same value was obtained even when using the latter column.

The distribution range of the molecular weight of the high molecular polysaccharide F-B specimen which was obtained from the culture materials of other strains was 7000 to 17000.

[High molecular polysaccharide F-Ab]

Figure 4B:
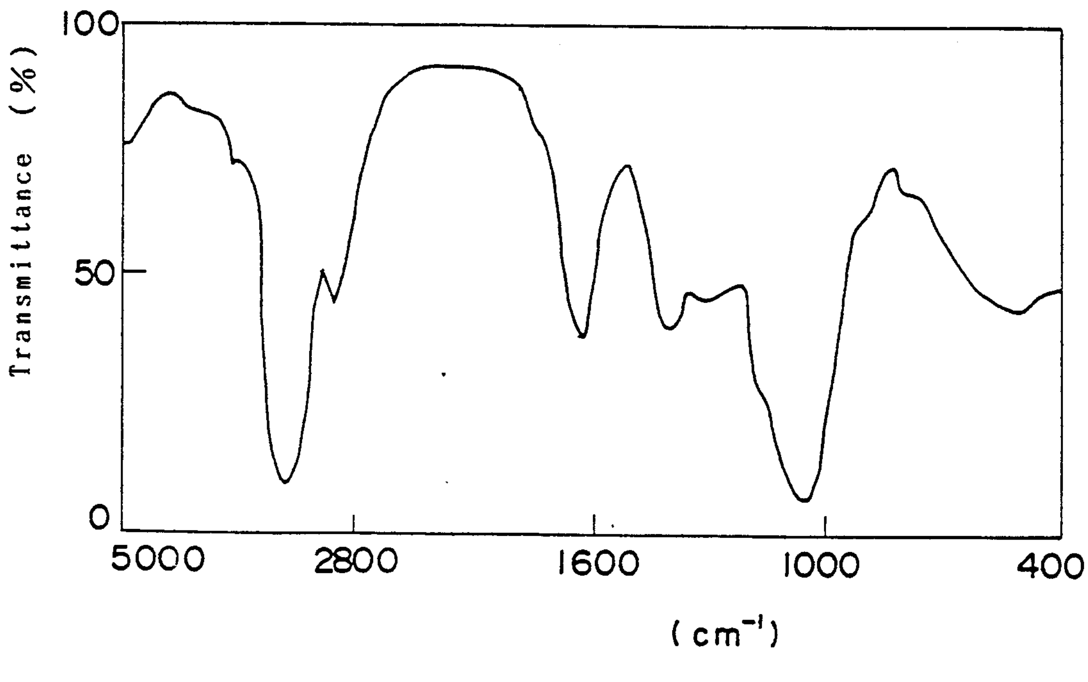
FIG. 4*b* shows the infrared absorption spectrum of the high molecular polysaccharide specimen salt F-Ab.

The infrared absorption spectrum of the high molecular polysaccharide F-Ab specimen salt which was obtained in (4) above, as shown on FIG. 4*b*, showed the strong absorption of —COO− of 1612 $cm^{-1}$ and contained cation such as sod'um ion.

Removing cation from the high molecular polysaccharide F-Ab specimen salt through an ion exchange resin column, the absorption of 1612 $cm^{-1}$ lessened; on the other hand, that of —COOH of 1725 $cm^{-1}$ was apparently shown.

Figure 5B:
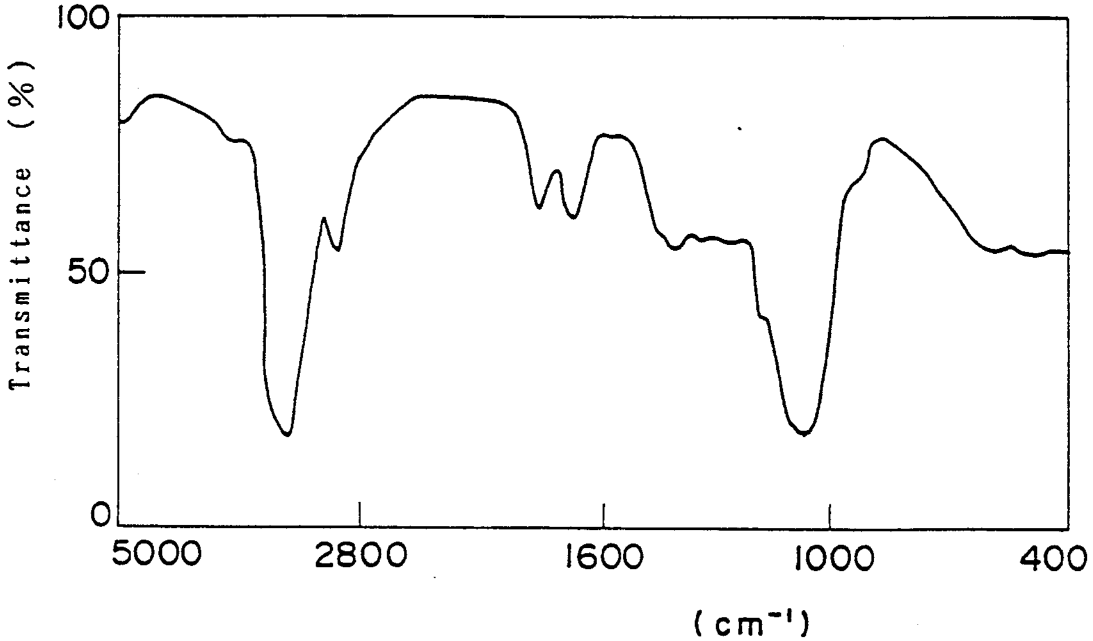
FIG. 5*b* shows the infrared absorption spectrum of the high molecular polysaccharide specimen F-Ab.

According to the infrared absorption spectrum, however, it is quite difficult to remove cation completely. Therefore, the purified specimen, as shown on FIG. 5*b*, was assumed to be high molecular polysaccharide F-Ab specimen.

These specimens obtained are apparently confirmed as a single material as a result of the aforementioned variety of chromatography. They were all white and became transparent when dissolved in water.

(a) Elementary analysis

Analytical results of high molecular polysaccharide F-Ab specimen salt which was obtained from the culture material of *Fomes fomentarius* JTS 3046 strain in (2) and (4) above are as follows.

C: 36.0%
H: 6.0%
N: 0.5%
Ash content: 9.0%

Analytical results of high molecular polysaccharide F-Ab specimen are as follows.

C: 37.9%
H: 5.9%
N: 0.4%
Ash content: 3.9%

In the above analysis, if the same tested samples are used, the values of N and Ash content often fluctuated. In this fluctuation, the values of C and H also fluctuated slightly.

It is assumed that the fluctuation of the quantity of Ash content, such as the ammonium ions and the sodium ions which combine to form salt, differed in every purification because high molecular polysaccharide F-Ab is acidic material.

In addition, because of the removal rate of cation by ion exchange resin changes in every experiment, the complete removal of N and Ash content could not be performed.

(b) Molecular weight determination

Figure 1B:
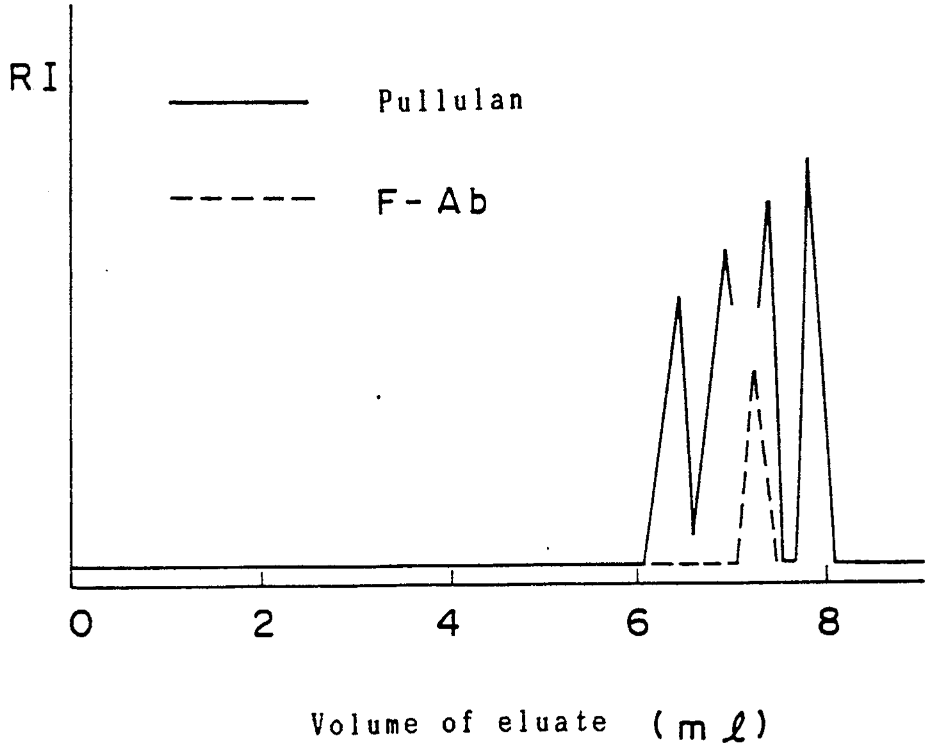
FIG. 1*b* shows the gel filtering chromatogram of the high molecular polysaccharide F-Ab in using TSK gel G3000 PWXL column. In the figure, a solid line shows molecular weight standard material pullulan, and a dotted line shows high molecular polysaccharide F-Ab.
Figure 2B:
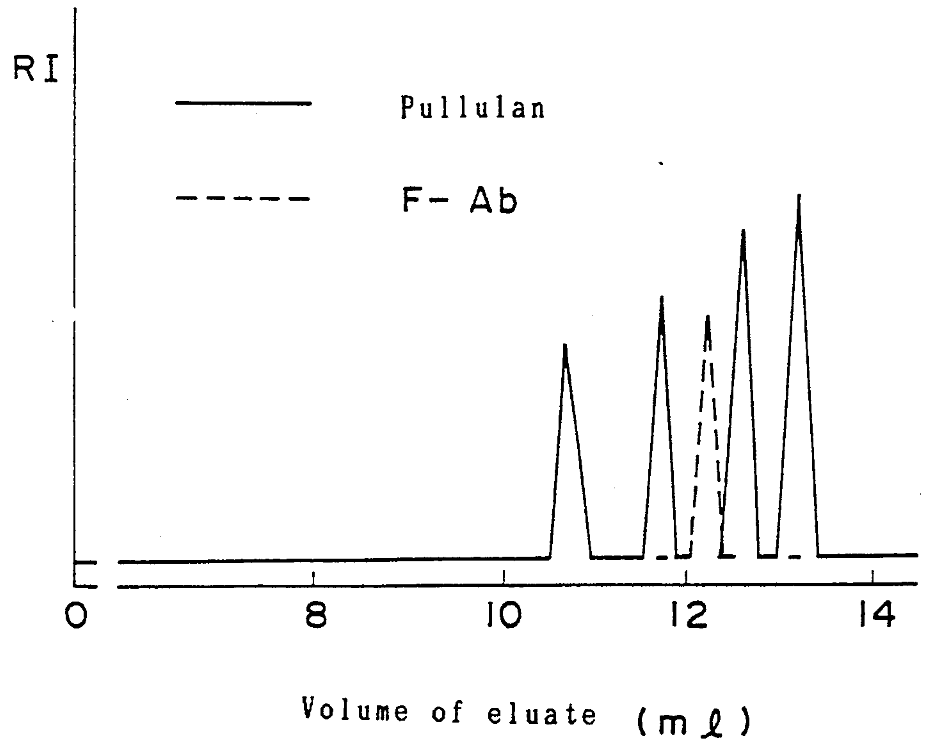
FIG. 2*b* shows the gel filtering chromatogram of the high molecular polysaccharide F-Ab in using Asahipak GS-510 column. In the figure, a solid line shows molecular weight standard material pullulan, and a dotted line shows high molecular polysaccharide F-Ab.
Figure 3A:
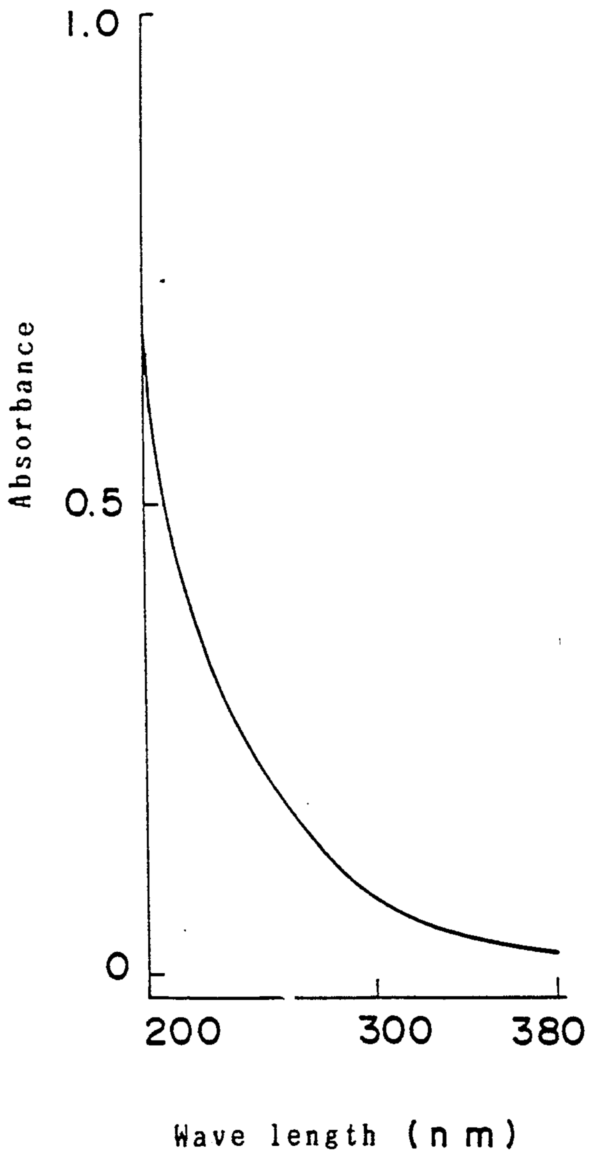
FIG. 3*a* shows the ultraviolet absorption spectrum of the high molecular polysaccharide F-B.
Figure 3B:
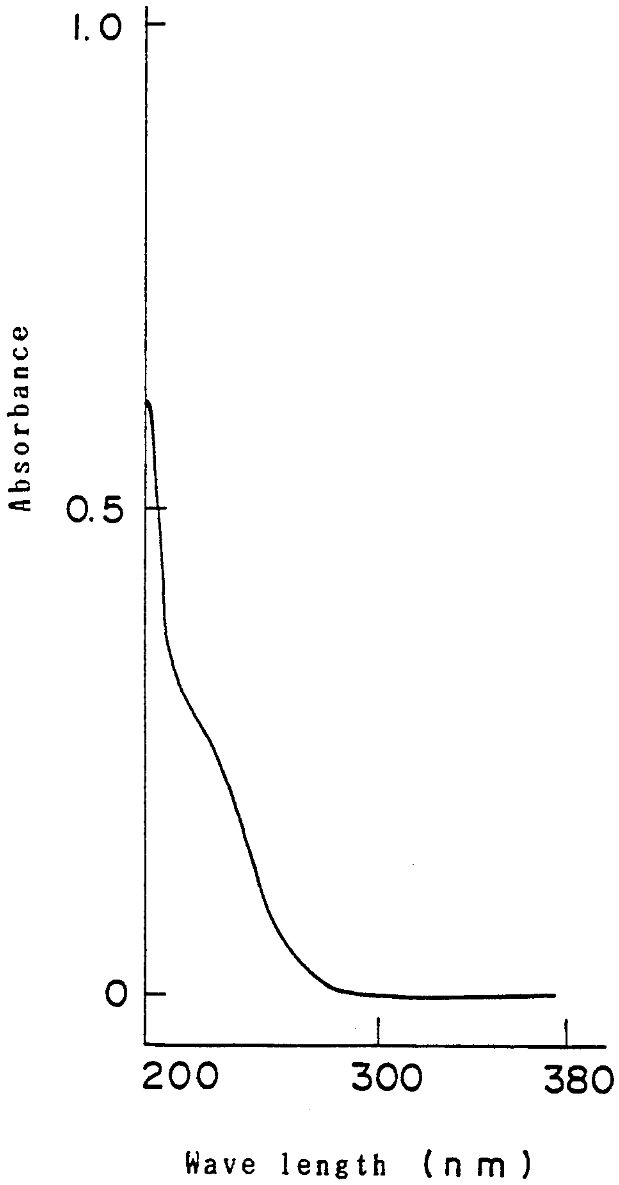
FIG. 3*b* shows the ultraviolet absorption spectrum of the high molecular polysaccharide F-Ab.

Test results of molecular weight of high molecular polysaccharide F-Ab, which was obtained from *Fomes fomentarius* JTS 3046 strain by gel filtration chromatography are shown on FIGS. 1*b* and 2*b*. Toso's TSK gel G3000 PWXL column or Asahikasei's Asahipak GS-510 column are equipped with high-speed liquid chromatography (attached to RI detector) and used pullulan as the standard molecular weight material (Pullulan Shodex STANDARD P-82; produced by Showadenko Co., Ltd.).

The distribution range of molecular weight by a gel filtration method was 10000—20000, and the mean molecular weight was 15500 in the former column and 16500 in the latter column.

The distribution range of the molecular weight of high molecular polysaccharide F-Ab specimen which was obtained from culture materials of other strains such as *Fomes fomentarius* IFO 8246, IFO 30371, ATCC 26708, etc., was also 10000—20000.

(6) Test samples

The following explanations are shown as test samples as to the effectiveness of a plant protection and virus removal chemicals according to the present invention.

[Test sample 1]

The anti-viral activities of the culture filtrate of various strains which was obtained in (1) above and its diluent water were examined in each TMV.

Tobacco species (Xanthin NC) which developed local lesions due to inoculating viruses were used in the test.

Tobacco plants for the test were cultivated in a pot with a 12 cm diameter. Six leaves in two pots (three leaves in each bowl) were tested as a sample.

In reference to the tested leaf, an opened leaf was bordered by the center vein (both upper surface and under surface of the leaf can be used), and a half of the leaf was coated with a tested liquid using a paintbrush. The other half of the leaf was coated with water for control.

One day after the sample was treated, the entire upper surface of the leaf was sprinkled with carborundum and purified TMV (0.05 μg/ml) was minutely inoculated.

Three or four days after the virus inoculation, the number of lesions which appeared on the inoculated leaf were counted, and the prevention rate was calculated using the following formula. The test results are shown on Table 1.

$$\text{Inhibition ratio } (\%) = \left(1 - \frac{\text{number of lesions on treated half}}{\text{number of lesions on control half}}\right) \times 100$$

TABLE 1

(Plant virus inhibition effectiveness of fungi)

| Tested fungi | Culture filtrate (Dilution rate) | Treatment | Inhibition ratio (%) |
|---|---|---|---|
| *Fomes fomentarius* | 200 | Upper surface coated | 100 |
| JTS 3046 | 10 | Under surface coated | 86 |
| *Fomes fomentarius* | 20 | Upper surface coated | 100 |
| IFO 8246 | 1 | Under surface coated | 87 |
| *Fomes fomentarius* | 20 | Upper surface coated | 98 |
| IFO 30371 | 1 | Under surface coated | 72 |
| *Fomes fomentarius* | 20 | Upper surface coated | 96 |
| ATCC 26708 | 1 | Under surface coated | 33 |
| *Fomes geotropus* | 10 | Upper surface coated | 100 |
| ATCC 26709 | 1 | Under surface coated | 56 |
| *Fomes melanoporus* | 10 | Upper surface coated | 95 |
| ATCC 26132 | 1 | Under surface coated | 32 |

As shown on Table 1, there was approximately 100% inhibition ratio on almost all tested samples where the upper surface of the leaf was treated.

[Test Sample 2]

The anti-viral activities of the culture filtrate of *Fomes fomentarius* JTS 3046 strain which was shown at the highest effectiveness in the test sample 1 and its diluent water was more minutely examined in TMV. The method which was used was in accordance with that of test sample 1. The test results are shown in Tables 2 and 3.

TABLE 2

(Plant virus inhibition effectiveness of culture filtrate; No. 1)

| Concentration Sample* | Coated Surface of Sample | Inoculated Surface | Number of lesions/ half leaf** Treated half | Untreated half | Inhibition Ratio (%) |
|---|---|---|---|---|---|
| 1 Dilution*** | Upper surface of half leaves | Upper surface of a leaf | 0.2 | 17.8 | 98.9 |
| 9 Dilutions | Upper surface of half leaves | Upper surface of a leaf | 0.2 | 65.0 | 99.7 |
| 30 Dilutions | Upper surface of half leaves | Upper surface of a leaf | 0.8 | 79.3 | 99.0 |
| 90 Dilutions | Upper surface of half leaves | Upper surface of a leaf | 1.8 | 128.7 | 98.6 |
| 100 Dilutions | Upper surface of half leaves | Upper surface of a leaf | 3.3 | 136.0 | 97.6 |
| 200 Dilutions | Upper surface of half leaves | Upper surface of a leaf | 6.3 | 290.3 | 97.8 |
| Distilled Water (Control) | Upper surface of half leaves | Upper surface of a leaf | 278.2 | 280.3 | 0.7 |

*Concentration of culture filtrate diluted in distilled water

**Mean value of number of lesions of 6 leaves

***Culture filtrate

TABLE 3

(Plant virus inhibition effectiveness of culture filtrate; No. 2)

| Concentration Sample* | Coated Surface of Sample | Inoculated Surface | Number of lesions/half leaf** Treated half | Number of lesions/half leaf** Untreated half | Inhibition Ratio (%) |
|---|---|---|---|---|---|
| 1 Dilution*** | Under surface of half leaves | Upper surface of a leaf | 1.3 | 54.0 | 97.6 |
| 9 Dilutions | Under surface of half leaves | Upper surface of a leaf | 16.2 | 104.5 | 84.5 |
| 30 Dilutions | Under surface of half leaves | Upper surface of a leaf | 40.2 | 208.3 | 80.7 |
| 90 Dilutions | Under surface of half leaves | Upper surface of a leaf | 49.2 | 177.8 | 72.3 |
| 100 Dilutions | Under surface of half leaves | Upper surface of a leaf | 93.7 | 142.0 | 34.0 |
| 200 Dilutions | Under surface of half leaves | Upper surface of a leaf | 87.3 | 128.5 | 32.0 |
| Distilled Water (Control) | Under surface of half leaves | Upper surface of a leaf | 238.2 | 246.7 | 3.4 |

*Concentration of culture filtrate diluted in distilled water
**Mean value of number of lesions of 6 leaves
***Culture filtrate As shown on Table 2, for the leaves treated on the upper surface, all tested samples showed approximately 100% inhibition ratio.

On the other hand, as shown on Table 3, inhibition ratio was proven as well, when the under surface of the leaf was treated. Also, even the untreated half of the leaf was affected.

In other words, compared with a leaf on which viruses were inoculated without coating any tested sample, there were a significant number less necrotic lesion on the control leaf half which was coated as the test sample.

These results show that the active materials were systemically effective in the present invention.

[Test sample 3]

Culture filtrate of Fomes fomentarius JTS 3046 strain was put in a dialysis membrane (Spectrobore 3). After the complete dialysis using water as an outer liquid, the culture filtrate was performed by Japan Analysis Industry's LC-09 model type extracted liquid chromatrography with columns using the inner liquid of the membrane. These columns have Asahipak GS-510 which is connected to GS-320 in a series. The inner liquid of the dialysis membrane was extracted using a 50 mM phosphate buffer solution (pH 7.0), and then neutral high molecular polysaccharide whose molecular weight is more than or equal to 0.1 million (approximately 200 mg/filtrate 1,000 ml) and acid high molecular polysaccharide whose molecular weight is less than or equal to 0.1 million (approximately 100 mg/filtrate 1,000 ml) were obtained.

In addition, tests of the culture filtrate, neutral high molecular polysaccharide and acid high molecular polysaccharide were performed in the same way as for test sample 1.

On the other hand, 5 lower leaves of the tobacco plant (Xanthin NC) of 55 days after seeding, height of 45 cm, were scattered by the culture filtrate and high molecular polysaccharide which had been obtained by the culture filtrate. A day later, three upper closed leaves were minutely inoculated with 0.05 μg/ml of TMV.

Distilled water was scattered in the area of the untreated control part.

Three or four days after the TMV inoculation, necrotic lesions which appeared on inoculated leaves were counted, and the inhibition ratio was calculated in the same way as for the test sample 1. The results are shown on Tables 4 and 5.

TABLE 4

(Plant virus inhibition effectiveness of culture filtrate and high molecular polysaccharide)

| Sample | Concentration | Coated Surface of Sample | Inoculated Surface | Inhibition Ratio (%) |
|---|---|---|---|---|
| Culture filtrate | No change | Upper surface of half leaves | Upper surface of a leaf | 100 |
| | | Under surface of half leaves | Upper surface of a leaf | 92 |
| Neutral high molecular polysaccharide | 200 μg/ml | Upper surface of half leaves | Upper surface of a leaf | 82 |
| | | Under surface of half | Upper surface of a leaf | 0 |

TABLE 4-continued (Plant virus inhibition effectiveness of culture filtrate and high molecular polysaccharide)

| Sample | Concentration | Coated Surface of Sample | Inoculated Surface | Inhibition Ratio (%) |
|---|---|---|---|---|
| | | leaves | | |
| Acid high molecular polysaccharide | 100 μg/ml of half | Upper surface of a leaf leaves | Upper surface | 100 |
| | | Under surface of half leaves | Upper surface of a leaf | 91 |

TABLE 5

(Systemic inhibition effectiveness of culture filtate and high molecular polysaccharide)

| Distinguished Sample | Concentration | Number of lesions/leaf | Inhibition Ratio (%) |
|---|---|---|---|
| Distilled Water (Control) | — | 439 | 0 |
| Culture filtrate | No change | 140 | 68 |
| Neutral high molecular polysaccharide | 200 μg/ml | 409 | 7 |
| Acid high molecular polysaccharide | 100 μg/ml | 124 | 53 |

As shown on Tables 4 and 5, the inhibition effectiveness works on the half leaf with no treatment. Additionally, the treatment by culture filtrate and acid high molecular polysaccharide on part of the tobacco leaf reduces the number of necrotic lesions in the upper half of the leaf which is not treated.

From the above, it can be concluded that the effectiveness of the culture filtrate and acid high molecular polysaccharide is systemic. From the checked result, it can also be considered that the systemic and effective substance in the culture filtrate is acid high molecular polysaccharide.

[Test Sample 4]

The culture filtrate of *Fomes fomentarius* JTS 3046 strain as a reagent and the anti-viral activity against TMV was tested using various plants.

The virus was used according to tested plants.

The culture filtrate was diluted into a moderate concentration by water and distributed. The virus was coated and inoculated the first day after distributing. The disease was investigated on the fourteenth day after inoculating. The result is shown on Table 6.

TABLE 6

(Plant virus inhibition effectiveness of culture filtrate concerning various plants)

| Checked plants (race) | Concentration (times) | Virus disease preventive action (number of non-disease/number of samples) | Disease rate in non-treated areas |
|---|---|---|---|
| Green pepper (*Fushimi amanaga*) | 2.5* | 7/10 | 70% |
| Green pepper (Shin-sakigake) | 5 | 5/10 | 70% |
| Tomato (Fukuju) | 5 | 5/10 | 70% |
| Tomato (Ponte Rosa) | 5 | 10/10 | 70% |

TABLE 6-continued (Plant virus inhibition effectiveness of culture filtrate concerning various plants)

| Checked plants (race) | Concentration (times) | Virus disease preventive action (number of non-disease/number of samples) | Disease rate in non-treated areas |
|---|---|---|---|
| Tobacco (Matsukawa) | 10 | 10/10 | 100% |
| Tobacco (Virginia 115) | 10 | 10/10 | 90% |
| Tobacco (Coker 319) | 10 | 10/10 | 100% |
| Tobacco (Coker 319) | 20 | 8/10 | 100% |
| Tobacco (MC1) | 5 | 10/10 | 100% |
| Tobacco (Bright yellow) | 2.5 | 6/10 | 100% |

*2.5 dilution by culture filtrate

The effectiveness was recognized not only in the combination of Xanthin NC and TMV, but also in combinations with other plants and TMV.

[Test Sample 5]

The filtration of hypha culture in *Fomes fomentarius* JTS 3046 strain produced culture filtrate and fungi.

While anti-viral activity in this culture filtrate was checked in the TMV, various high molecular polysaccharides, high molecular polysaccharide F-B and high molecular polysaccharide F-Ab were examined.

The tobacco species (Xanthin NC) which developed local necrotic lesions due to the inoculating viruses were used in the test.

The tobacco plants for the test were cultivated in a pot with a 12 cm diameter.

An opened leaf was bordered by the center vein (both upper surface and under surface of the leaf can be used), and a half of the leaf was coated with a tested liquid using a paintbrush. The other half of the leaf was coated with water for control.

One day after treatment, the entire upper surface of the leaf was inoculated with the virus.

The concentration of inoculation virus was 0.05 μg/ml of TMV.

The number of necrotic lesions which appeared on the inoculated leaf were counted on the third through seventh days after inoculation. The inhibition ratio was calculated using the formula for the sample in Test 1.

The results are shown on Tables 7, 8, 9, and 10.

TABLE 7

(Plant virus inhibition effectiveness from various extractions)

| Sample Extraction | Concentration | Coated Surface of Sample | Inoculated Surface | Inhibition Ratio (%) |
|---|---|---|---|---|
| Culture Filtrate | No change | Upper surface of half leaves | Upper surface of a leaf | 100 |
| | | Under surface of half leaves | Upper surface of a leaf | 92 |
| High molecular polysaccharide F-N | 200 μg/ml | Upper surface of half leaves | Upper surface of a leaf | 82 |
| | | Under surface of half leaves | Upper surface of a leaf | 0 |

TABLE 7-continued (Plant virus inhibition effectiveness from various extractions)

| Sample Extraction | Concentration | Coated Surface of Sample | Inoculated Surface | Inhibition Ratio (%) |
|---|---|---|---|---|
| High molecular polysaccharide F-Ab | 100 μg/ml | Upper surface of half leaves | Upper surface of a leaf | 100 |
| | | Under surface of half leaves | Upper surface of a leaf | 89 |
| High molecular polysaccharide F-B | 100 μg/ml | Upper surface of half leaves | Upper surface of a leaf | 100 |
| | | Under surface of half leaves | Upper surface of a leaf | 82 |
| High molecular polysaccharide F-C | 100 μg/ml | Upper surface of half leaves | Upper surface of a leaf | 97 |
| | | Under surface of half leaves | Upper surface of a leaf | 76 |

TABLE 8

(Plant virus inhibition effectiveness of high molecular polysaccharide F-B)

| Concentration Sample | Coated Surface of Sample | Inoculated Surface | Number of lesions/half leaf* Treated Half | Untreated Half | Inhibition Ratio (%) |
|---|---|---|---|---|---|
| 200 μg/ml | Under surface of half leaves | Upper surface of a leaf | 0.3 | 14.2 | 97.9 |
| 100 μg/ml | Under surface of half leaves | Upper surface of a leaf | 5.2 | 27.8 | 81.2 |
| 10 μg/ml | Under surface of half leaves | Upper surface of a leaf | 20.0 | 67.8 | 70.5 |
| 0 μg/ml | Under surface of half leaves | Upper surface of a leaf | 106 | 118 | 10.1 |

*Mean value of number of lesions of 6 leaves

TABLE 9

(Plant virus inhibition effectiveness of high molecular polysaccharide F-Ab; No. 1)

| Concentration Sample | Coated Surface of Sample | Inoculated Surface | Number of lesions/half leaf* Treated Half | Untreated Half | Inhibition Ratio (%) |
|---|---|---|---|---|---|
| 200 μg/ml | Upper surface of half leaves | Upper surface of a leaf | 0 | 18.7 | 100 |
| 100 μg/ml | Upper surface of half leaves | Upper surface of a leaf | 0.2 | 65 | 99.7 |
| 10 μg/ml | Upper surface of half leaves | Upper surface of a leaf | 3.3 | 136 | 97.6 |
| 0 μg/ml | Upper surface of half leaves | Upper surface of a leaf | 284 | 290 | 2.0 |

*Mean value of number of lesions of 6 leaves

TABLE 10

| (Plant virus inhibition effectiveness of high molecular polysaccharide F-Ab; No. 2) | | | | | |
|---|---|---|---|---|---|
| | Coated | | Number of lesions/ half leaf* | | |
| Concentration Sample | Surface of Sample | Inoculated Surface | Treated Half | Untreated Half | Inhibition Ratio (%) |
| 200 μg/ml | Under surface of half leaves | Upper surface of a leaf | 1.5 | 16.7 | 91.0 |
| 100 μg/ml | Under surface of half leaves | Upper surface of a leaf | 3.3 | 26.7 | 87.6 |
| 10 μg/ml | Under surface of half leaves | Upper surface of a leaf | 14.7 | 62.8 | 76.6 |
| 0 μg/ml | Under surface of half leaves | Upper surface of a leaf | 136 | 128 | 2.0 |

*Mean value of number of lesions of 6 leaves

According to Tables 7 and 9, for the leaves treated on the upper surface, almost all tested samples showed close to a 100% inhibition ratio.

According to Tables 8 and 10, treatment with acid high molecular polysaccharide F-B, acid high molecular polysaccharide F-Ab or culture filtrate thereof, showed effectiveness not only in the inhibition ratio even for the under surface of the leaf, but it also showed effectiveness on the untreated leaf half.

In other words, compared with a leaf on which viruses were inoculated without coating any tested sample, there were a significant number less necrotic lesions on the contrasted leaf half which was coated over the test sample.

These results show that both acid high molecular polysaccharide F-B and acid high molecular polysaccharide F-Ab were systemically effective in the present invention.

[Test Sample 6]

On the other hand, 5 lower leaves of the tobacco plant (Xanthin NC) of 60 days after seeding, height of 45 cm, were scattered by the culture filtrate and high molecular polysaccharide which had been obtained by the culture filtrate. A day later, three upper closed leaves were minutely inoculated with 0.05 μg/ml of TMV.

Distilled water was scattered in the area of the untreated control part.

Three days after the TMV inoculation, necrotic lesions which appeared on inoculated leaves were counted, and the inhibition ratio was calculated in the same way as for the test sample 1. The results are shown on Table 11.

TABLE 11

| (Systemic inhibition effectiveness of various extractions) | | | |
|---|---|---|---|
| Distinguished Sample | Concentration | Number of lesions/leaf | Inhibition Ratio (%) |
| Distilled Water (Control) | — | 439 | 0 |
| Culture filtrate | No change | 140 | 68 |
| High molecular polysaccharide F-N | 200 μg/ml | 409 | 7 |
| High molecular polysaccharide F-Ab | 100 μg/ml | 124 | 72 |
| High molecular polysaccharide F-B | 100 μg/ml | 211 | 52 |
| High molecular polysaccharide F-C | 100 μg/ml | 283 | 35 |

As shown on Table 11, it can be concluded that the effectiveness of this activated ingredient is systemic from the fact that the number of lesions decreased even in a non-treated leaf of identical individual organisms owning to the treatment of a part of the tobacco's leaves using this activated ingredient.

We claim:

1. A composition for the protection of plants from viruses which consists essentially of a carrier and polysaccharide F-B, having the following chemical properties, as an effective ingredient:

(a) elementary analysis

[high molecular] polysaccharide F-B specimen salt

C: 34.8%

H: 5.5%

N: 0.6%

Ash content: 11.6%

[high molecular] polysaccharide F-B specimen

C: 37.1%

H: 5.9%

N: 0.5% ash content: 5.2%

(b) molecular weight range of molecular weights according to the gel filtration method: 7000-17000 daltons mean molecular weight according to the gel filtration method: 12000 daltons (c) sugar composition and its constitution glucose: glucuronic acid=3.4:1;

wherein said polysaccharide is produced by a fungus selected from the group consisting of *Fomes fomentarius* IFO 8246, IFO 30371, IFO 30777, ATCC 26708, ATCC 34687, ATCC 46213, FERM BP-2230, *Fomes geotropus* ATCC 26709, and *Fomes melanoporous* ATCC 26132.

2. The composition according to claim 1, wherein said fungus is *Fomes fomentarius* FERM BP-2230.

3. The composition according to claim 1, wherein said polysaccharide has the characteristics as shown in FIGS. 1*a*–5*a*.

4. A composition for the protection of plants from viruses which consists essentially of a carrier and polysaccharide F-Ab, having the following chemical properties, as an effective ingredient:

(a) elementary analysis polysaccharide F-Ab specimen salt

C: 36.0%
H: 6.0%
N: 0.5%
ash content: 9.0% polysaccharide F-Ab specimen

C: 37.9%
H: 5.9%
N: 0.4%
ash content: 3.9%

(b) molecular weight range of molecular weights according to the gel filtration method: 10000–20000 daltons mean molecular weight according to the gel filtration method: 15500–16500 daltons (c) sugar composition and its constitution glucose: glucuronic acid=9:2.0–1.8;

wherein said polysaccharide is produced by a fungus selected from the group consisting of *Fomes fomentarius* IFO 8246, IFO 30371, IFO 30777, ATCC 26708, ATCC 34687, ATCC 46213, FERM BP-2230, *Fomes geotropus* ATCC 26709, and *Fomes melanoporus* ATCC 26132.

5. The composition according to claim 4, wherein said polysaccharide has the characteristics as shown in FIGS. 1*b*–5*b*.

6. The composition according to claim 4, wherein said fungus *Fomes fomentarius* FERM BP-2230.

* * * * *